United States Patent [19]

Seufert

[11] Patent Number: 4,568,327
[45] Date of Patent: Feb. 4, 1986

[54] METHOD AND APPARATUS FOR THE REMOVAL OF GASES PHYSICALLY DISSOLVED BY DIALYSIS IN THE BLOOD

[75] Inventor: Wolf D. Seufert, Sherbrooke, Canada

[73] Assignee: Universite de Sherbrooke, Quebec, Canada

[21] Appl. No.: 583,733

[22] Filed: Feb. 27, 1984

[51] Int. Cl.$^4$ ............................................. A61M 37/00
[52] U.S. Cl. ........................................ 604/5; 210/646
[58] Field of Search ....................... 604/4, 5, 6, 27, 28, 604/29; 55/158, 159; 210/634, 645, 646

[56] References Cited

U.S. PATENT DOCUMENTS

| | | | |
|---|---|---|---|
| 3,994,799 | 11/1976 | Yao et al. ................................. | 604/5 |
| 4,001,141 | 12/1977 | Hyden et al. ............................ | 604/5 |
| 4,003,554 | 12/1977 | Willock et al. ....................... | 604/5 X |
| 4,127,481 | 11/1978 | Malchesky et al. ................. | 604/5 X |
| 4,303,068 | 12/1981 | Zelman ................................... | 604/5 |
| 4,410,338 | 10/1983 | Yamamoto et al. .................. | 55/158 |
| 4,439,217 | 3/1984 | Yamabe et al. ....................... | 55/158 |

Primary Examiner—John Doll
Assistant Examiner—Glenn A. Caldarola
Attorney, Agent, or Firm—Cushman, Darby & Cushman

[57] ABSTRACT

The disclosure herein describes a method and apparatus for the removal, by dialysis, of gases physically dissolved in the blood of a person, more particularly a diver or an aviator; the blood is brought into contact, in an exchange cell, with a membrane permeable to gases only; a liquid having high solubility for gases is circulated on the side of the membrane so that the gases dissolved in the blood are made to follow their chemical potential gradient across the membrane into the liquid.

10 Claims, 2 Drawing Figures

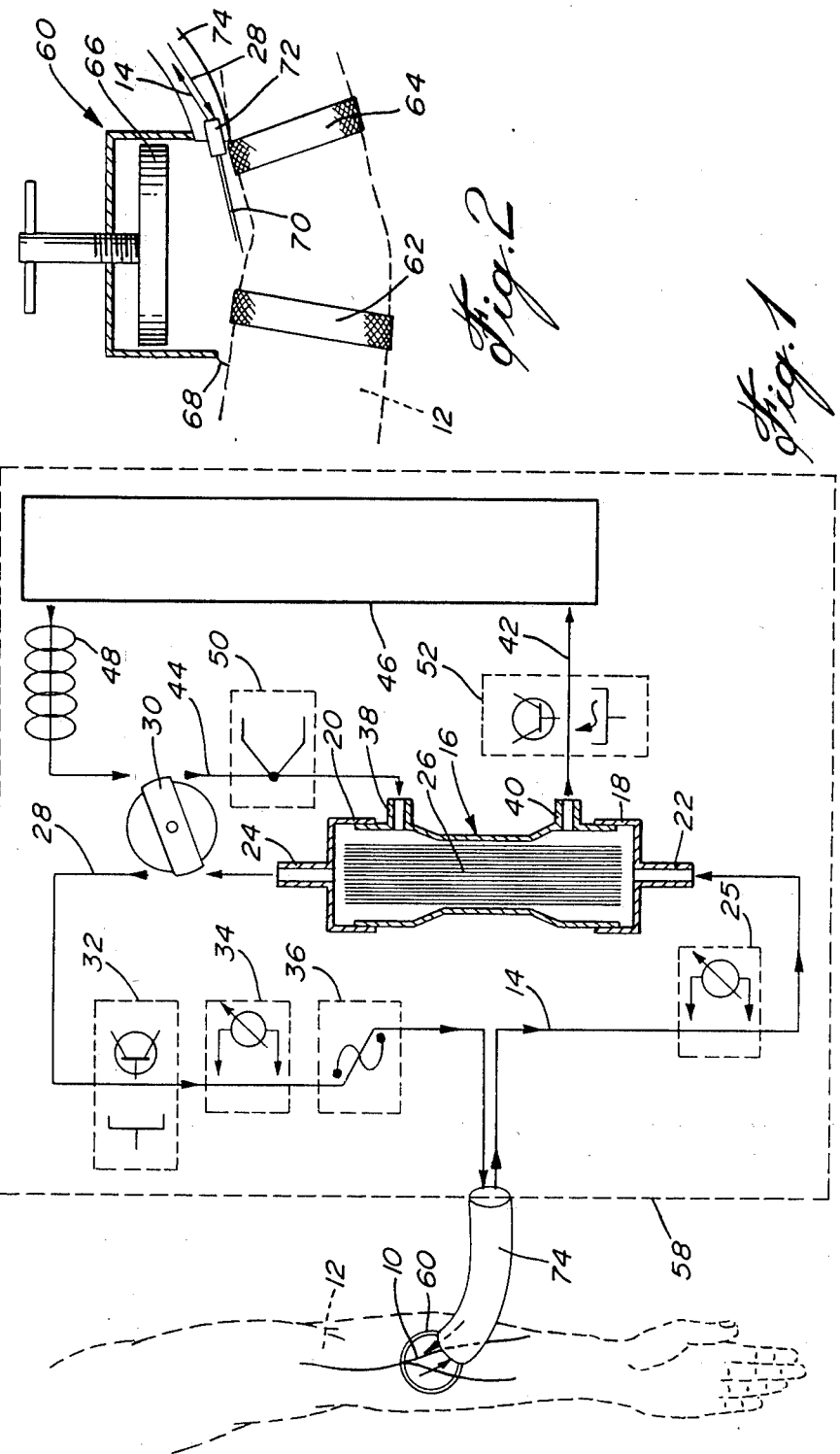

METHOD AND APPARATUS FOR THE REMOVAL OF GASES PHYSICALLY DISSOLVED BY DIALYSIS IN THE BLOOD

FIELD OF THE INVENTION

The present invention relates to a system for the removal of gases physically dissolved by dialysis in the blood of a person, more particularly a diver or an aviator.

BACKGROUND OF THE INVENTION

A diver has to breathe compressed air or a mixture of gases containing the appropriate amount of oxygen at a pressure equal to the hydrostatic pressure compressing the thorax, in order to be able to inflate the lungs. As the gas pressure is increased with the depth to which he descends, the quantity of gases physically dissolved in the blood plasma and the body tissues increases proportionally. While oxygen is metabolized, all other gases in the mixture will come out of solution again as soon as the hydrostatic pressure on the diver is reduced during his ascent to the surface. This decompression has to proceed at a very slow rate in order to prevent the occurrence of the phenomena seen when a bottle of a sparkling liquid is opened and its contents are abruptly decompressed: the dissolved gases are immediately released and coalesce to form bubbles. The gases that are not metabolized by the organism must be prevented from coming out of solution in this way since even small bubbles could block peripheral capillaries and thereby increase the load on the heart. In more serious cases, the gases form larger bubbles which can produce gas embolisms in the blood vessels of vital organs, infarctions and necroses of the surrounding tissues and will ultimately lead to death.

The clinical signs of decompression sickness following a too rapid ascent to the surface correspond to the accumulation of gas bubbles in the joints. The person so afflicted minimizes the load on his/her articulations and maintains a distorted or bent posture, thus 'the bends'. The later stages of decompression sickness are characterized by increasingly severe neurological disorders which are explained with functional losses in the central nervous system due to air embolisms.

Decompression sickness is prevented by requiring divers to follow a strict ascent schedule which takes into account the depth reached and the duration of stay at depth. Ascent tables have been established semi-empirically and are constantly revised as the knowledge of the various physical and physiological parameters determining the distribution of gases in blood and the tissues as a function of muscular activity increases. Replacing nitrogen in the respired air with helium, a gas that has a much lower solubility in the tissues, has somewhat reduced the incidence of decompression sickness but an accident at work might require an ascent too rapid to prevent the bends even under such a "Heliox" (trademark) atmosphere.

Divers brought to the surface too rapidly will always suffer from the bends to individually varying degrees. They will, in most cases, recuperate completely, i.e. without any apparent permanent lesions, if brought promptly into a recompression chamber where barometric pressure corresponding to the hydrostatic pressure at depth can be established and in which the slow ascent to the surface is simulated. Recompression chambers are very costly and are mainly found on land; only a few research vessels for deep-sea diving are so equipped. They are thus invariably located at considerable distances from the scene of a dive and the consequent delay in treatment increases the risk to the diver suffering from the symptoms of decompression sickness. Several symptomatic treatment schemes are available but they are only supplementary to recompression.

The deep-sea exploration for petroleum and the mining of minerals bring divers even further away from the few centers where a prompt and complete treatment of decompression sickness can be effected. Emergency recompression chambers found on off-shore drilling rigs, for example, are small mobile units in which a diver can be evacuated but in which he cannot be treated. Some accidents in underwater work require immediate medical attention and do not leave time for the elaborate ascent schedule that can last several hours or even several days. Incidents have been reported in which recompression treatment was delayed by hours with, subsequently, the diver's complete recovery, but the individual variations are great and these cases cannot be used to establish a therapeutic strategy. Decompression by bringing the diver back into the water is not meant to replace treatment in a chamber. At present, divers are all too often confronted with the alternative to succumb to an injury at depth subsequent to only a minor working accident, or, to suffer the consequence of a rapid decompression, with a real possibility to die from it.

The sudden failure of a pilot's pressurization equipment at altitude (explosive decompression) leads to the same phenomena and produces the same results.

OBJECTS AND STATEMENT OF THE INVENTION

It is an object of the present invention to provide a method and apparatus to eliminate gases physically dissolved in blood by dialysis in the treatment of decompression sickness of divers and aviators. As a result, the ascent time for divers can be reduced dramatically.

Blood from a cannulated vein is brought into contact with a membrane permeable to gases only and not to the blood plasma, to the formed elements of the blood, nor to any ions or molecules dissolved in it. The gases dissolved in the plasma are made to follow their chemical potential gradient across the membrane or film selectively permeable to them, into a liquid that has a very high solubility for them and extracts them from the blood by virtue of its affinity. A liquid characterized by its very high solubility for gases, typically a perfluorocarbon or a silicone, circulates on the side of the membrane opposite the blood.

The families of liquids prescribed for the present application have the highest uptake capacities for gases known. They are chemically inert and do not corrode or attack in any way the gas-permeable membrane, nor do they dissolve into it. They are not toxic and are, in fact, used in the formulation of 'artificial blood' to carry oxygen to the tissues. In the most efficient hemodialysis arrangement, blood and the dialyzate are pumped through the exchange cell in a countercurrent fashion.

Several polymers have been developed that permit the selective passage of gases. They are either of the solution-diffusion type, i.e., only those molecules soluble in the membrane itself can diffuse through it (examples: Silastic brand sheeting, Dow Corning, Mississauga, Ont.; dimethyl silicone, various types, General Electric, Schenectady, N.Y.), or, they permit the transfer of gases by the process of ultrafiltration, i.e., through exclusive pores. Vycor brand glass (Corning Glass Works, Elmira, N.Y.) is selectively permeable to gases by virtue of the fact that it contains pores with an average size of 40 Å and a very narrow size distribution. The materials mentioned are typical and have nitrogen permeabilities of, respectively, 110 (Silastic), 330 (Vycor) and 400 (silicone) ml per (min) (m$^2$) (atm). Vycor glass has the advantage that it could eventually be drawn into fine capillary tubing for the construction of 'hollow fiber' dialysis cartridges to present a very high exchange area. Perfluorocarbon liquids with a high and reversible uptake capacity for gases are available in a wide variety; typically, perfluorodecalin and perfluorotributylamine dissolve 28 ml nitrogen gas per 100 ml at temperatures between 25° and 35° C.

The apparatus intended to perform gas removal by dialysis according to the present invention consists of a gas exchange cell, also called a dialyzer, and ancillary equipment whose function is to maintain the relative fluid flows, to monitor the conditions pertaining to the gas exchange and, through feedback circuits, to keep the conditions within the range set.

Other objects and further scope of applicability of the present invention will become apparent from the detailed description given hereinafter. It should be understood, however, that this detailed description, while indicating preferred embodiments of the invention, is given by way of illustration only since various changes and modifications within the spirit and scope of the invention will become apparent to those skilled in the art.

BRIEF DESCRIPTION OF THE DRAWINGS

For a better understanding of the present invention, reference is had to the following description taken in connection with the accompanying drawings in which:

FIG. 1 is an over-all diagrammatic showing of an illustrative embodiment of the present invention; and FIG. 2 is a cross-sectional view of a cup showing the equipment used for the cannulation of a blood vessel under-water.

DESCRIPTION OF PREFERRED EMBODIMENTS

Referring to FIG. 1, blood is drawn from a cannulated vein 10 of a diver or aviator's arm 12 through a venous puncture. This is possible by the use, for example, of a commercially available single-access dual-flow catheter with a 18-gauge needle, as is securely used in clinical hemodialysis. Of course, conventional double-needle cannulas could also be used. The collected blood is transported through a conduit 14 to a gas exchange cell 16. The cell may consist of a cylindrically-shaped container which is sealingly closed at opposite ends by means of caps or manifolds 18 and 20, respectively provided with an inlet port 22 and an outlet port 24. Blood received in conduit 14 passes by an afferent flow monitor 25 to enter inlet port 22 and then passes through a plurality of hollow fibers 26, each fiber having a gas permeable membrane into a liquid having high uptake capacities for gases. The blood then exits at the outlet port 24 and is returned to the vein through conduit 28. Blood flow is supported by a pump 30. In the blood return conduit, an electronic air/foam detector 32 with a warning light is provided in order to stop pump 30 if a passing bubble changes the optical density in the conduit. An afferent flow monitor 34 is also provided in the return conduit as well as a further monitor 36 which is used to indicate the pressure of the blood being returned.

The exchange cell further includes an inlet port 38 and an outlet port 40 to allow the dialysis liquid to pass along membranes 26. Conduits 42 and 44 connect the inlet and outlet ports to a reservoir 46 containing the perfluorocarbon or silicone liquid. Pump 30 also serves to circulate the liquid between the reservoir 46 and the exchange cell 16. The liquid is brought to the body temperature by means of a heating element 48, controlled by a thermostat 50. On return to the reservoir, the optical absorbance of the liquid is monitored at 52, at the exit manifold, in order to detect possible blood leaks through the exchange surface.

The exchange surface in the hollow fiber cartridge should be as large as possible. Areas of up to 1.5 m$^2$ are typical for cartridges used in conventional hemodialysis. Cartridges about 40 cm long can hold enough fibers with a diameter of 200 micrometers to give an exchange area of more than 3 m$^2$. Several valves (not shown) permit to interrupt the flow safely; ports (not shown) are provided to inject heparin or other anticoagulants continuously.

The maximum volume of metabolically inert gas that dissolves in the body tissues hyperbaric conditions is estimated to be about 4.5 liters, a value extrapolated from measurements performed normobarically. Accordingly, the dialyzate reservoir should contain about 20 liters of perfluorocarbon liquid in order to maintain the appropriate partial pressure gradient with the blood at all times. In reality, the fluid volume can be much smaller than that since the release of nitrogen from the tissues is diffusion-limited and the 1 to 2 liters of circulating blood are rapidly cleared of gas. The apparatus illustrated schematically in FIG. 1 will easily fit into a portable canister 58 appropriately armoured to withstand the water pressure.

The equipment to be used for the cannulation of a blood vessel under water is shown in FIG. 2. A perspex cup 60 is attached to the bend of the arm by two straps 62 and 64 fixing it in an extended position. A piston 66 draws water out of the cup in order to establish a negative pressure with respect to the outside. This seals the cup with its cushioned rim 68 against the arm and makes the blood vessels under it stand out. The catheter and needle 70 enter the perspex cup at a shallow angle through a port 72, closed by a rubber membrane 74, to facilitate cannulation. The tubings, 14 and 28 from the cup to the canister containing the dialysis equipment is wrapped in a flexible armoured conduit 74.

Only about 5 vol % of the oxygen bound to hemoglobin inside the red blood cells is normally used up by the body so that the hemoglobin on the venous side still holds about 16 of the 21 vol % to which the blood is charged in the lungs. The small fraction of oxygen dissolved physically in the plasma is in equilibrium with that bound to hemoglobin in the erythrocytes and decompression dialysis will thus also reduce the amount of oxygen carried by the red blood cells. It is therefore recommended that persons undergoing decompression dialysis respire an atmosphere enhanced in oxygen. Before use, the apparatus for decompression dialysis is to be primed, on the blood side, with a degassed physiological saline solution and, on the side of the dialyzate, with the degassed perfluorocarbon liquid. This prevents that bubbles form in the tubing or that the procedure would be started with bubbles adhering to the surfaces.

Decompression dialysis as described will remove gases dissolved in the blood and the tissues of a diver much faster than they can be passed through the lungs during the slow ascent in stages prescribed by International Diving Tables. As a consequence, divers can be brought to the surface rapidly in an emergency, without suffering the effects of decompression sickness, or, suffering them to a much lesser extent. Conceivably, many lives may be saved which are otherwise lost due to the fact that recompression facilities are not immediately at hand. The principles involved in decompression dialysis are simple and the apparatus required is far from complicated so that the divers themselves could be instructed in its use at the surface or even under water as a first-aid measure. The process of hemodialysis started at depth can then continue above the surface.

Decompression dialysis could also be used as a preventive measure to extent the diving times which are, at present, limited by the long ascent periods more than by the degree of physical exertion at depth. This application would require, of course, that divers submit to the inconvenience of having a vein cannulated before the dive, to permit prompt access to the dialysis equipment.

The embodiments of the invention in which an exclusive property or privilege is claimed are defined as follows:

1. A method for the removal, by dialysis, of gases physically dissolved in the blood of a person, such as a diver or an aviator, comprising the steps of:

bringing the blood from a cannulated vein of the person into contact in an exchange cell with a membrane permeable to gases only; and circulating a liquid having high solubility for gases on the side of said membrane whereby the gases dissolved in the blood are made to follow their chemical potential gradient across said membrane into said liquid.

2. A method as defined in claim 1, wherein the circulation of the liquid is done countercurrent to the blood flow.

3. A method as defined in claim 1, wherein said liquid is a perfluorocarbon liquid.

4. A method as defined in claim 3, wherein said liquid is perfluorodecalin.

5. A method as defined in claim 3, wherein said liquid is perfluorotributylamine.

6. A method as defined in claim 1, wherein said liquid is a silicone.

7. A method as defined in claim 1, wherein the blood and the liquid are pumped through the exchange cell.

8. A method as defined in claim 1, further comprising the step of monitoring the flow of blood between the cannulated vein and the membrane.

9. A method as defined in claim 1, further comprising the step of monitoring the liquid as it circulates on the side of the membrane.

10. A method as defined in claim 9, further comprising heating said liquid to a temperature corresponding substantially to that of said blood.

* * * * *